(12) United States Patent
Bonutti

(10) Patent No.: US 11,737,878 B2
(45) Date of Patent: Aug. 29, 2023

(54) IMPLANT COMPRISING NONBIOLOGIC PORTION AND BIOLOGIC PORTION

(71) Applicant: P Tech, LLC, Effingham, IL (US)

(72) Inventor: Peter M. Bonutti, Manalapan, FL (US)

(73) Assignee: P TECH, LLC, Manalapan, FL (US)

( * ) Notice: Subject to any disclaimer, the term of this patent is extended or adjusted under 35 U.S.C. 154(b) by 0 days.

(21) Appl. No.: 15/382,105

(22) Filed: Dec. 16, 2016

(65) Prior Publication Data

US 2017/0172743 A1 Jun. 22, 2017

Related U.S. Application Data

(60) Provisional application No. 62/268,308, filed on Dec. 16, 2015.

(51) Int. Cl.
| | |
|---|---|
| *A61F 2/28* | (2006.01) |
| *A61L 27/56* | (2006.01) |
| *A61L 27/36* | (2006.01) |
| *A61L 27/04* | (2006.01) |
| *A61F 2/30* | (2006.01) |

(52) U.S. Cl.
CPC ............ *A61F 2/2846* (2013.01); *A61L 27/04* (2013.01); *A61L 27/3612* (2013.01); *A61L 27/56* (2013.01); *A61F 2002/2835* (2013.01); *A61F 2002/3092* (2013.01); *A61F 2002/3093* (2013.01); *A61L 2430/02* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,758,643 | B2 * | 7/2010 | Stone ..................... | A61F 2/28 623/14.12 |
| 2005/0049706 | A1 * | 3/2005 | Brodke ............... | A61F 2/30767 623/17.11 |
| 2005/0272153 | A1 * | 12/2005 | Xuenong ................ | A61L 27/00 435/395 |
| 2006/0105015 | A1 * | 5/2006 | Perla ...................... | A61L 27/32 424/423 |
| 2009/0005868 | A1 * | 1/2009 | Gundlapalli .......... | A61F 2/4644 623/11.11 |

* cited by examiner

*Primary Examiner* — Yashita Sharma
(74) *Attorney, Agent, or Firm* — Stinson LLP

(57) ABSTRACT

In one aspect, an implant for replacing subject tissue includes a nonbiologic portion and a biologic portion grown on the nonbiologic portion. The biologic portion may be grown on the nonbiologic portion before being implanted in the subject. The nonbiologic portion may comprise a porous metal substrate (e.g., scaffolding). The nonbiologic portion may be formed by 3D printing (i.e., additive manufacturing). The nonbiologic portion may be patient-specific. A robot may be used to shape the implant before implantation and/or to shape bone being replaced/resurfaced.

12 Claims, 14 Drawing Sheets

X-Ray

MRI

CT Scan

IMPLANT COMPRISING NONBIOLOGIC PORTION AND BIOLOGIC PORTION

CROSS REFERENCE TO RELATED APPLICATIONS

This application claims priority to U.S. Provisional Patent Application Ser. No. 62/268,308, which is hereby incorporated by reference in its entirety.

FIELD OF THE DISCLOSURE

The present disclosure generally relates to an implant comprising a nonbiologic portion and a biologic portion grown on the nonbiologic portion.

BACKGROUND OF THE DISCLOSURE

Implants or grafts can be used to repair or replace broken or missing bone or other regenerative tissues. Implants are typically formed of biologic materials that encourage tissue growth in the cells of one or both of the implant material and the host tissue. Some implants are configured to be resorbed by the host tissue, and prior to being resorbed lack the structural characteristics of the host tissue.

SUMMARY OF THE DISCLOSURE

In one aspect, an implant for replacing subject tissue includes a nonbiologic portion and a biologic portion grown on the nonbiologic portion. The biologic portion may be grown on the nonbiologic portion before being implanted in the subject. The nonbiologic portion may comprise a porous metal substrate (e.g., scaffolding). The nonbiologic portion may be formed by 3D printing (i.e., additive manufacturing). The nonbiologic portion may be patient-specific. A robot may be used to shape the implant before implantation and/or to shape bone being replaced/resurfaced.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
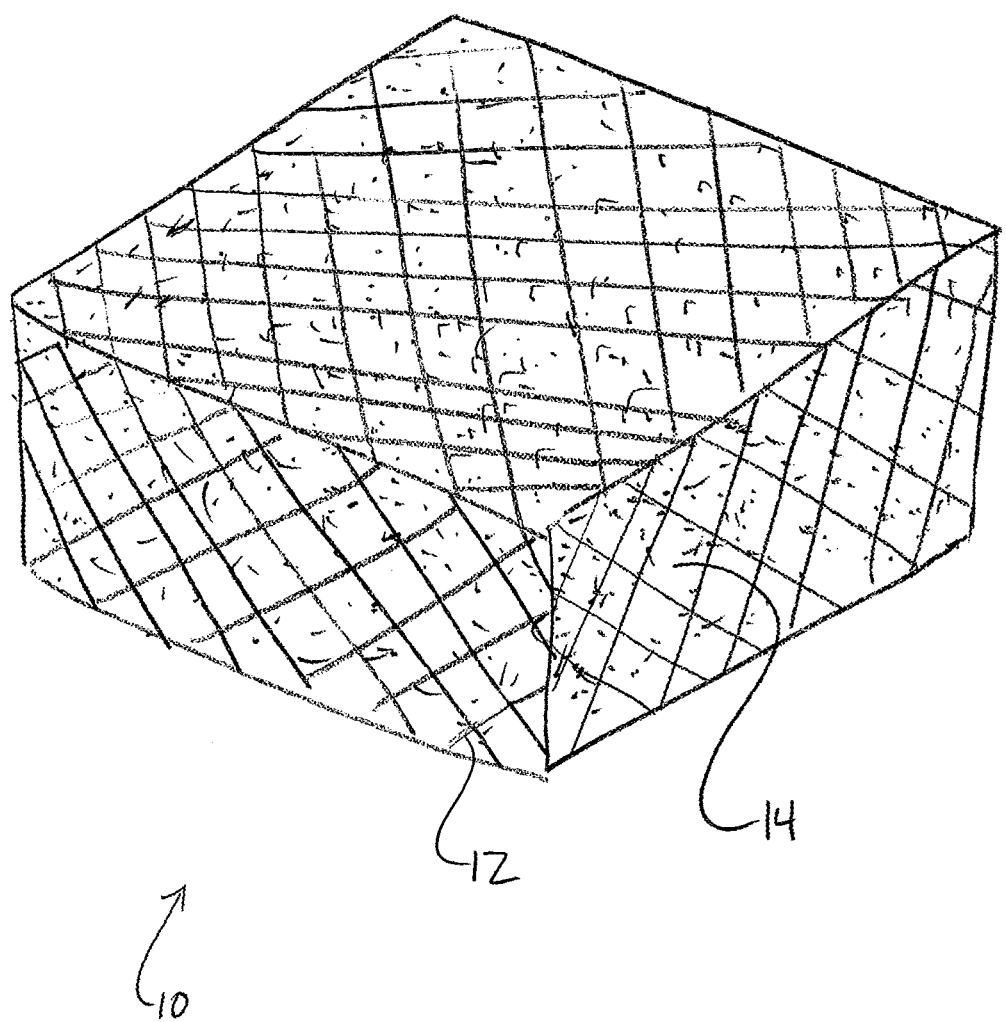
FIG. 1 is a schematic perspective of one embodiment of an implant.

Referring to FIG. 1, one embodiment of an implant for being grafted into tissue of a subject (e.g., a human or animal subject) is generally indicated at reference number 10. The implant 10 comprises a nonbiologic portion 12 (shown schematically with crosshatching) and a biologic portion 14 (shown schematically with stippling). In the illustrated embodiment, the implant 10 is configured for being implanted in bone tissue of a subject for use as a bone graft, but other embodiments can be configured for being implanted into other types of tissues (e.g., muscle tissue, tendon tissue, pancreatic tissue, kidney tissue, vascular tissue, nerve tissue, retinal tissue, other eye tissue, cardiac tissue, brain tissue, etc.). The implant 10 may include features of the implants discussed in U.S. Pat. No. 7,299,805, which is hereby incorporated by reference in its entirety. The illustrated implant 10 may be used to replace a portion of subject bone that is removed during surgery or missing due to injury. The implant can, likewise, be used as a plug for a focal defect or to replace a whole condyle or section of bone. The nonbiologic portion 12 comprises a three-dimensional structure that is configured to be self-supporting and configured to support the biologic portion 14 thereupon. The biologic portion 14 is compatible with subject bone for repairing or replacing the damaged bone tissue through, for example, osteoconduction, osteoinduction, osteopromotion and/or osteogenesis of the tissue. The implant is configured to be implanted into the subject, whereby the nonbiologic portion 12 provides an immediate load bearing structural repair of the tissue and the biologic portion 14 promotes regenerative and/or reparative tissue growth.

The nonbiologic portion 12 (e.g., scaffold) may be specifically designed and constructed to facilitate growth of the biologic portion and the host tissue thereon. The nonbiologic portion 12 forms a shell (e.g., scaffold) comprising an engineered porous metal, foam metal, a porous polymer, a foamed polymer (e.g., PEEK), or other nonbiologic material or materials, such as synthetic hydroxyapatite over a metal core porous, foam, or textured metal. To promote tissue ingrowth on the surface of the nonbiologic shell 12, the shell may be formed from a biodegradable material, such as PLA/PGA, etc., which is degradable into acidic compound. If the shell is made of these materials, the biodegradable components may be alkalinized for more accurate tissue ingrowth. Various metals (e.g., titanium) can provide a high strength substrate for the implant 10 that is chemically compatible to the subject biologic environment after implantation. Polymers can also be chemically compatible to the subject biologic environment and can be configured to have dynamic properties (e.g., flexibility, resilience, etc.) that correspond with the dynamic properties of the subject tissue. Polymer materials may also be preferred where the likelihood of subsequent surgical procedures being performed at the implant site is high because they can be operated on using standard surgical tools.

The porous or foamed nonbiologic materials 12 are shaped and arranged for supporting the biologic material 14 for incubation thereupon and for receiving ingrown tissue that interdigitates with the shell when the implant is surgically inserted into the subject tissue. In one or more embodiments, the shell 12 is formed by 3D printing (e.g., additive manufacturing). As explained below, using additive manufacturing of the shell 12 allows the shell to be custom-manufactured to match the characteristics of the subject tissue. However, other manufacturing processes such as foaming, machining (e.g., milling), etc., may also be used to form the shell in other embodiments. In one or more embodiments, the shell 12 receives biologic growth-enhancing materials after being formed. For example, hormones, enyzmes, or other growth-enhancing materials are deposited on the shell 12 to promote growth of the biologic material 14 and/or the host tissue through the network of pores in the shell.

In certain embodiments, the biologic portion 14 is grown (e.g., in an incubator) on the shell 12 before implantation in the subject. Various biologic materials may be used depending on the subject host tissue that is being repaired or replaced. For example, autologous cells, allogenic cells, xenograft cells, stem cells, tissue inductive factors, and/or fat cells can be placed on the shell 12 and these biologic materials are grown on the shell inside an incubator to form the implant 10. Stem cells, in particular, may be harvested from placentas, embryos, and/or newborn tissue samples and stored in tissue banks until they are needed for an implant. Precursor cells could, for example, be collected from newborn and placental tissue samples at hospital births as a matter of course and stored for subsequent use in treating a subject or a subject's family members using an implant 10 whose biologic material 14 is incubated from the precursor cells. As described in U.S. Pat. No. 8,641,660 and U.S. Patent Application Publication No. 2013/0190682, each of which is hereby incorporated by reference in its entirety, various conditions of the materials and/or microclimate of the incubation system can be controlled to promote incubation of the biologic portion 14 in the shell 12. For example, the microclimate in the incubation system can be controlled for, inter alia, oxygen tension, temperature, pH, and osmolarity, to enhance biologic growth during incubation.

Figure 13C:
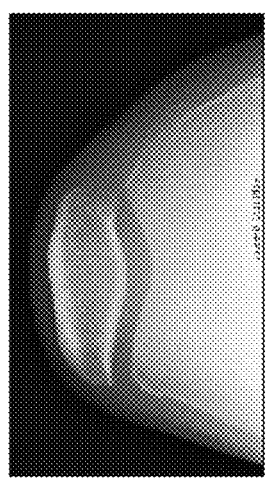
FIG. 13C is an x-ray of a subject knee.
Figure 13B:
FIG. 13B is an MRI of a subject knee.
Figure 13A:
FIG. 13A is a CT scan of a subject knee.

After the biologic portion 12 of the implant 10 is formed, the implant may be stored until it is needed for a surgical procedure. After manufacture or shortly before implantation, the implant 10 may be packaged in sterilized packaging (not shown) and stored in conditions that preserve the viability of the biologic portion 14. The packaged implant 10 is delivered in its sterilized packaging to the surgical site. At the surgical site, the surgeon images the host bone tissue prior to implantation. For example, the surgeon can image the host bone tissue using MRI, CT (e.g., mars CT), ultrasound, x-ray, PET, or any other suitable imaging technology. Example images from a CT scan, an MRI, and an X-ray of a subject knee are shown in FIGS. 13A-13C. The surgeon uses the imaging to determine the size and shape of the implant region of the bone tissue. For example, the surgeon can determine the contours of the perimeter of the bone tissue at the implantation site. Determining the size and shape of the implant region can be performed automatically using three-dimensional modeling software based on the image data. In addition, as explained below, the surgeon can use the imaging to determine other properties of the subject tissue, such as porosity and density, and use the determined properties to match the properties of the implant to those of the subject tissue. After imaging the tissue and evaluating the implant region, the surgeon prepares the implant 10 and the implant region of the host tissue for implantation. In some subjects, metal artifacts in the subject may render imaging data unreliable. To provide more reliable imaging data, multiple imaging techniques may be performed in combination and their data compiled to eliminate errors. When information about the size, shape, porosity, etc. of the subject tissue is unavailable after preoperative imaging, the surgeon can make inferences about the subject tissue based on other known biometric parameters of the subject and/or other known biologic models. For example, in symmetrical tissue, such as the hip joint, the surgeon can infer the geometry about one side of the hip joint that is concealed from imaging by a metal artifact from image data about the opposite side of the hip joint.

Preparing the host tissue for implantation can comprise shaping the host tissue for receiving the implant 10. For example, in one embodiment, a surgical robot (e.g., a ROSA surgical robot, a MAKO surgical robot, a da Vinci surgical robot, etc.) or another surgical implement is used to remove a portion of the subject bone to shape the host tissue for receiving the implant 10. Preparing the implant 10 for implantation can likewise comprise shaping the implant to correspond with the shape of the implant region of the host tissue. A surgical robot or another shaping tool (e.g., a milling machine, etc.) can be used to shape the implant 10 to correspond with the implant region of the host tissue 10. For example, in one or more embodiments, the host tissue and the implant 10 are respectively shaped for forming a press-fit connection. Specifically, the host tissue could be shaped to define a tapered hole (e.g., a conical hole), and the implant 10 could be shaped to define a correspondingly tapered perimeter surface. As explained below, additional attachment structure may also be used to connect the implant 10 to the host tissue in certain embodiments. Shaping can be done preoperatively (e.g., remote for the operating room) or during the implantation procedure. In addition to shaping the host tissue and the implant 10, preparing for implantation can include depositing one or more tissue growth enhancing agents at one or both of the implantation region of the host tissue and the implant.

When the host tissue and the implant 10 are prepared for implantation, the surgeon surgically places the implant on the host tissue. For example, the surgeon either manually, or using a surgical robot, mounts the implant 10 on the bone so as to establish a biological connection between the biologic material 14 and the host tissue. The implant 10 may also be mounted on the bone to establish a structural connection between the shell 12 and the host tissue, whereby the shell becomes a load bearing portion of the subject skeletal structure. In one embodiment, the implant 10 is mounted on the host tissue by a press fit connection. If the press fit connection 10 does not provide enough strength, the connection can be reinforced using a wire binding, a fastener (discussed below), a pressure type device (e.g., a pneumatic sleeve, an elastic sleeve), etc. After implantation, through osteogenesis, osteopromotion, osteoinduction, and/or osteoconduction, tissue that is connected to the host tissue is ingrown into the shell 12 and the shell is grafted into the host tissue. In some embodiments, the host tissue resorbs the biologic material 14 as it grows through the pores of the shell 12. The shell 12 may not be resorbed in some embodiments and instead becomes permanently interdigitated with the subject bone.

When preparing the subject tissue for implantation and implanting the implant 10 into the subject, various types of surgical robots may be used. Suitable surgical robots for preparing the implant 10 and target tissue for implantation, as well as installing the implant 10 in the subject tissue, are described in U.S. Pat. Nos. 6,770,878 and 9,155,544, each of which is hereby incorporated by reference in its entirety. In one embodiment, a free-floating surgical robot that suspends itself in the body of the subject and includes a drive system for navigating through the body of the subject is used. Such a robot may, for example be driven through the body of the subject to the implant site using an external electromagnetic field. Free-floating surgical robots can navigate through the body of the subject using prime locations as reference markers. The prime locations can provide references that are fixed with respect to certain anatomical features of the subject to account for any movement of the subject during the operation. The prime locations can be identified using reflective markers or other markers that are placed in the body of the subject. For example, the markers can be placed at desired locations in the body based on a preoperatively determined robot guidance route that is determined based on preoperative imaging of the subject body. The location of the robot in the subject body can be monitored using a rigid tracker mounted on the robot and/or the implant. Suitable surgical navigation techniques are described in U.S. patent application Ser. No. 15/299,981, which was filed on Oct. 21, 2016, and is hereby incorporated by reference in its entirety. Robots that are fixed in place in the operating room and include one or more robotic surgical arms may also be used in some embodiments. In some embodiments, the surgical robots are fully automated; in other embodiments they are surgeon-controlled (e.g., using haptic feedback, etc.). Visualization for a surgeon-controlled robot may be provided by direct visualization of the surgical site, endoscopic visualization, magnetic visualization, ultrasound visualization, etc. In one or more embodiments, the surgical robot is directly linked to the body part of the patient receiving the implant 10 to control motion of the body part. For example, the surgical robot can be configured to control flexion, extension, rotation, etc., during the procedure.

Figure 2:
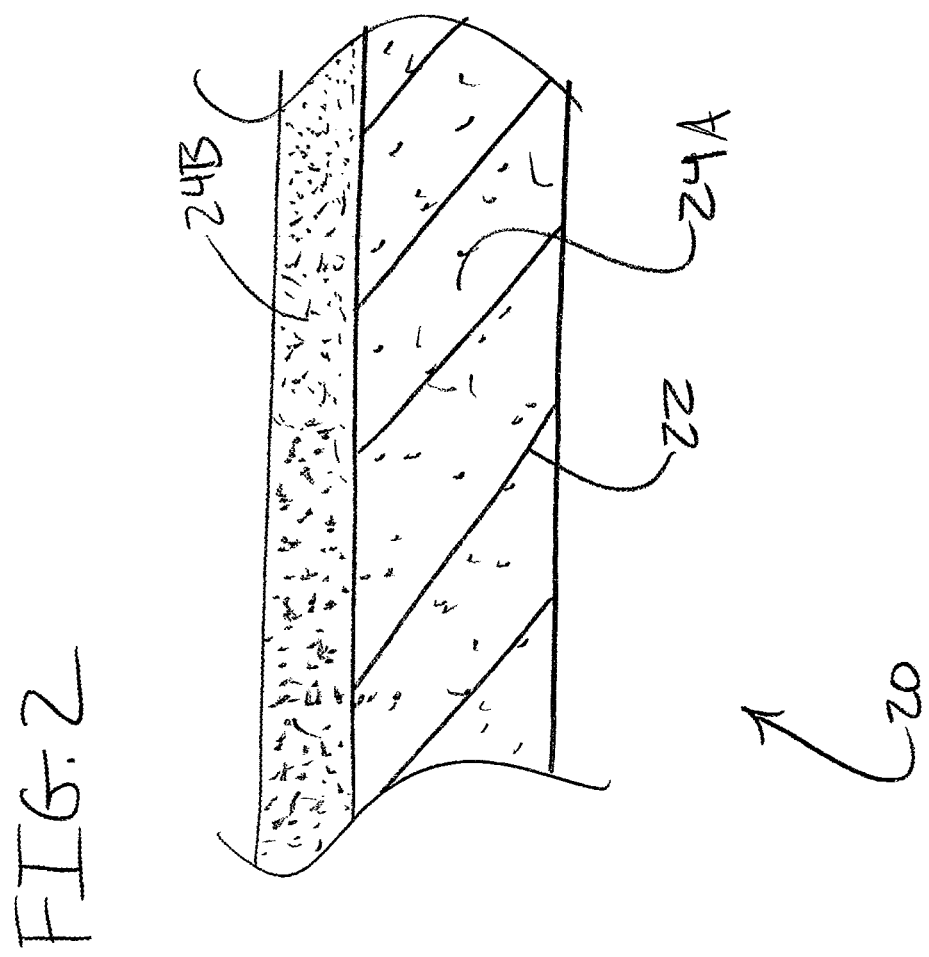
FIG. 2 is a fragmentary schematic cross section of one embodiment of an implant for replacing an articular surface of a joint.

Referring to FIG. 2, another embodiment of an implant that is configured for replacing an articular surface of a joint is generally indicated at reference number 20. Aspects of joint surgery that may be included during an operation to place the implant 20 in a joint of a subject are described in U.S. Pat. No. 7,635,390, which is hereby incorporated by reference in its entirety. Like the implant 10, the implant 20 includes a nonbiologic shell 22 and a biologic portion 24. The nonbiologic shell 22 is formed of porous nonbiologic material as explained above. As also explained above, the biologic portion 24 of the implant 20 includes a bone part 24A that is incubated to grow in the pores of the shell 22 for forming a bone graft with host bone in a subject. In addition, the illustrated biologic portion 24 of the implant includes a cartilage part 24B that is grown on the bone part. Like the bone part 24A, the cartilage part 24B is suitably grown in an incubator. The bone part 24A is grown into the shell 22 and the cartilage part 24B is grown on top of the bone part. Suitably, the cartilage part 24B is grown to have a thickness that matches the articular cartilage thickness of the joint that is to be resurfaced or repaired using the articular implant 20. For example, the patella articular cartilage is up to 1 centimeter thick and is thicker than the articular surface of the femur which may only be 5 millimeters thick.

In one or more embodiments, prior to implanting the implant 20 into a joint portion of a bone, the surgeon measures the thickness of the articular cartilage of the host bone at the implant location. For example, using the imaging techniques described above, the surgeon can measure the thickness of the articular cartilage at the implant location. The implant 20 is formed (e.g., incubated) to have a cartilage part 24B that is substantially the same thickness as the measured thickness of the host bone. For example, in one embodiment, the thickness of the articular cartilage of the host bone is measured before the cartilage part 24B is incubated so that the cartilage part can be grown to the desired thickness. In another embodiment, before the measurement is taken, the implant 20 is formed to have a cartilage part 24B that is substantially thicker than a normal thickness for the type of bone that is being repaired. Material from the cartilage part 24B may thus be removed at the surgical site to match the thickness (and shape) of the cartilage part with the thickness (and shape) of the articular cartilage of the host bone. In still another embodiment, a plurality of implants 20 having cartilage parts 24B of varying thicknesses are manufactured before the thickness of the articular cartilage of the subject is measured (e.g., a plurality of articular implants are manufactured and stored in an implant bank). The surgeon selects one of the plurality of implants 20 that comprises a cartilage part 24B of about the same thickness as the measured thickness for implanting in the subject. As explained above, before implanting the implant 20 in the subject, the surgeon may shape the implant for matching the implant region of the host bone. Since the implant 20 is configured to define an articular surface of the host bone, the step of shaping the implant suitably comprises shaping the cartilage part to define a surface that corresponds (e.g., has generally contiguous and uniform contours with) the articular surface of the host bone.

Figure 3:
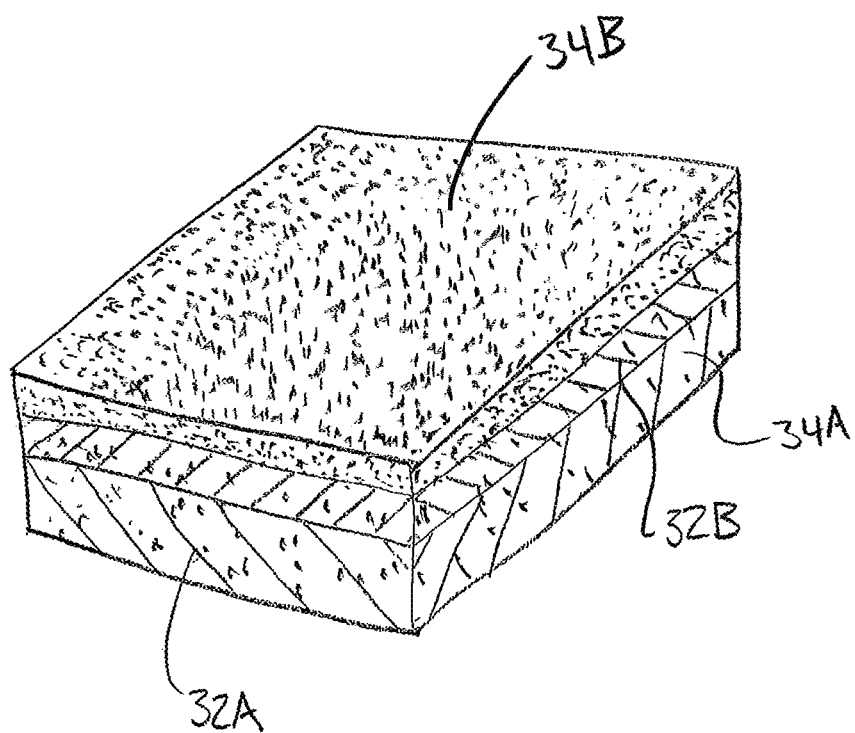
FIG. 3 is a schematic perspective of another embodiment of an implant for replacing an articular surface of a joint.

Referring to FIG. 3, another embodiment of an implant suitable for replacing an articular surface of a joint is generally indicated at reference number 30. Like the implants 10, 20, the implant 30 includes a nonbiologic portion 32 and a biologic portion 34. In the illustrated embodiment, the nonbiologic portion 32 includes a first layer 32A having a first porosity and a second layer 32B having a second porosity. The first layer 32A is sized and arranged for being received in the cancellous bone of the subject, while the second layer 32B is sized and arranged for being received in the cortical bone of the subject. For example, the thickness of the cortical layer of the subject bone is measured using, e.g., the imaging techniques discussed above (note that porosity and other three-dimensional characteristics of the tissue can be determined from the image data shown in FIGS. 13A-13C based on the color of the image), and the shell 30 is manufactured so that the low porosity layer 32B has about the same thickness as the measured thickness of the cortical layer. The high porosity portion of the shell 32A suitably has about the same porosity as the cancellous portion of the subject bone and the low porosity portion 32B suitably has about the same porosity as the cortical bone and subchondral plate of the subject bone. A biologic bone material 34A is embedded into the first layer 32A and the second layer 32B of the nonbiologic shell 32 as explained above, and in the illustrated embodiment a cartilage part 34B is grown on the bone part, above the nonbiologic shell. The implant 30 can be shaped to form a press fit connection with the host bone and to define a perimeter surface that corresponds in a contiguous manner with the shape of the perimeter (e.g., articular surface) of the host bone. When the implant 30 is press fit into the subject bone, the cartilage part 34B is aligned with the subject cartilage, the low porosity portion 32B of the shell 32 is aligned with the cortical bone of the subject, and the high porosity part 32A is aligned with the cancellous bone of the subject.

Although the shell layers 32A, 32B (broadly, shell regions) are described above as differing from one another in porosity, shell regions may also differ from one another in other ways that are controllable using additive manufacturing techniques. For example, in one or more embodiments, a nonbiologic shell comprises regions formed of different materials. Suitably, the materials chosen for the different regions of the shell are selected because they have material characteristics that correspond with tissue regions of the subject into which they are being implanted. In other embodiments, a nonbiologic shell comprises regions formed of materials of different densities, orientations, etc. Again, such characteristics are suitably chosen to correspond with corresponding tissue regions in the subject.

Figure 4:
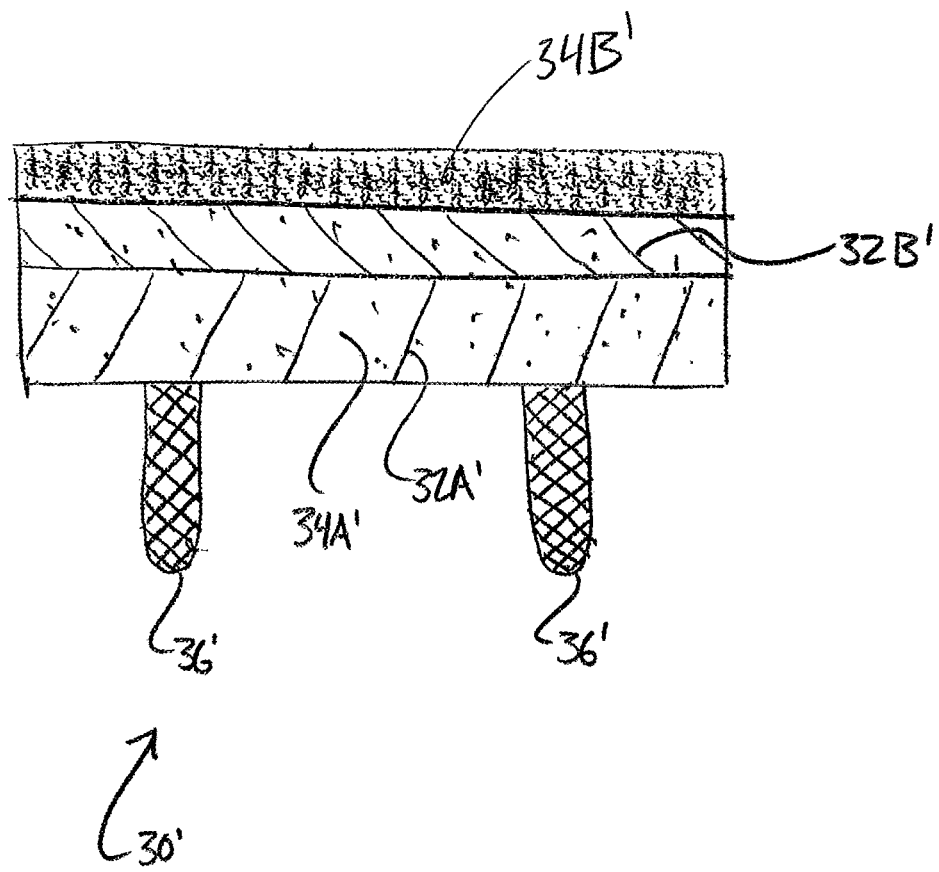
FIG. 4 is a schematic elevation of another embodiment of an implant for replacing an articular surface of a joint.

Referring to FIG. 4, another embodiment of an implant suitable for replacing an articular surface of a joint is generally indicated at reference number 30'. Like the implant 30, the implant 30' comprises a nonbiologic shell 32' that includes a high porosity layer 32A' and a low porosity layer 32B', along with biologic material 34' including a bone part 34A' imbedded in the shell and a cartilage part 34B' supported on the bone part. In addition, the implant 30' includes one or more keels 36' (broadly, anchoring projections) for anchoring the implant in the host tissue. In the illustrated embodiment, the implant include two keels 36' that protrude from spaced apart locations along a perimeter surface of the high porosity layer 32A' of the shell 32' for being received in the cancellous bone of the subject. Other embodiments can include other numbers and arrangements of keels. In some embodiments, the keels 36' may be formed contiguously with the shell 32' (e.g., in a single 3D printing operation) and from the same material. The keels 36' can also be formed to have lower porosity than other portions of the shell 32' to provide the keels with greater structural strength and rigidity for anchoring the implant 30' in the subject bone.

Before inserting the implant 30' into the subject bone tissue, the bone tissue is prepared for receiving the keels 36'. Specifically, the bone tissue is prepared by boring first and second anchoring holes in the bone tissue that are sized and arranged for receiving the keels 36' to form a press fit, close tolerance fit, interference fit, or the like. The keels 36' securely anchor the implant 30' in the bone tissue to enhance the strength of the connection between the implant and the bone. The keels 36' provide fixation of the implant 30' to the host tissue before ingrowth of the host tissue into the shell 32' can occur. The keels 36' can be configured for receiving tissue ingrowth after implantation occurs to further enhance the connection with the host tissue.

Figure 5:
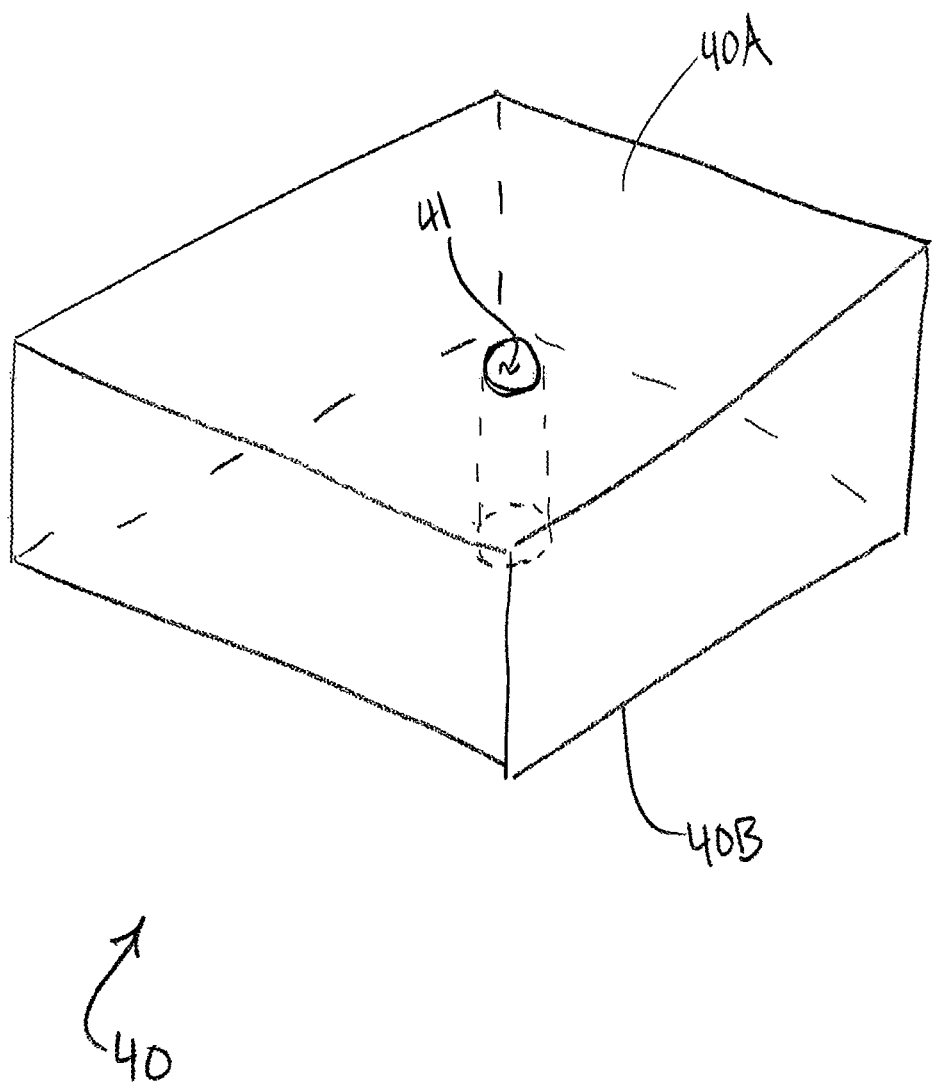
FIG. 5 is schematic perspective of another embodiment of an implant.

Referring to FIG. 5, another embodiment of an implant for replacing a portion of subject tissue is generally indicated at 40. Like the implant 10, the implant 40 suitably comprises a nonbiologic porous shell and a biologic material configured for forming a graft with the subject tissue embedded in the shell. (The nonbiologic shell and the biologic material are not shown schematically as in the drawings discussed above in order to more clearly illustrate other features of the implant 40.) In the illustrated embodiment, a mounting hole 41 is formed in the implant 10. The mounting hole 41 can be formed during an additive manufacturing process used to construct the nonbiologic shell or in a subsequent boring process (broadly, material removal process). The illustrated mounting hole 41 extends from an outer surface 40A of the implant 40 (which may in some embodiments comprise incubated cartilage as described above) to an inner surface 40B of the implant. The mounting hole 41 is sized and arranged for receiving a tissue fastener such as a bone screw, sutures, or the like, which extends through the mounting hole in use to fasten the implant 40 to the subject tissue. In certain embodiments, a portion of the nonbiologic shell of the implant 40 immediately adjacent the mounting opening 41 has a lower porosity and/or higher strength than other portions of the implant to provide cladding for receiving a screw that threads or taps itself into the implant. In other embodiments, the portion of the nonbiologic shell of the implant 40 immediately adjacent the mounting opening 41 is internally threaded for threadably receiving a screw. Other implants could have other numbers and arrangements of mounting holes in other embodiments. For example, in implants for replacing an articular surface of a joint and other types of implants, it is expressly contemplated that the mounting hole can extend from a side surface through the interior surface 40B at an inclined angle so that the fastener does not interfere with the cartilage part of the tissue which may form a bearing surface in the subject joint.

Figure 6:
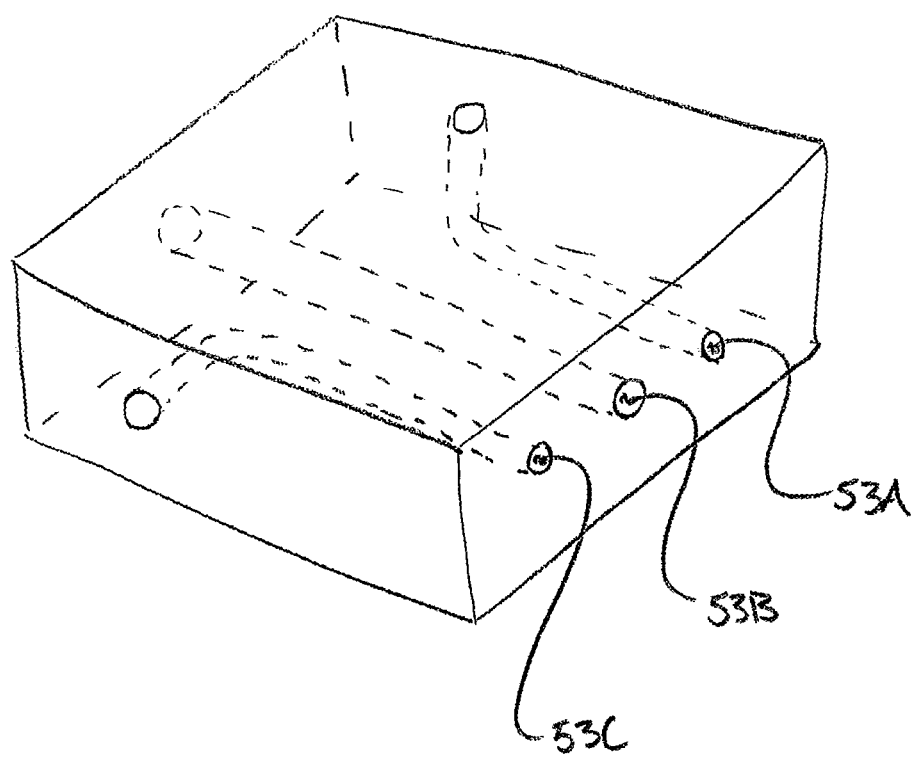
FIG. 6 is schematic perspective of another embodiment of an implant.

Referring to FIG. 6, another embodiment of an implant for replacing a portion of subject tissue is generally indicated at 50. The implant 50 comprises a nonbiologic porous shell and a biologic material configured for forming a graft with the subject tissue embedded in the shell. (Neither of these aspects of the implant is schematically illustrated in FIG. 6 in order to more clearly show other features of the implant 50.) The illustrated implant 50 includes a plurality of elongate passages 53A-53C for receiving elongate structures of the subject body. When the implant 50 is surgically inserted into the subject tissue, each passage 53A-53C is configured to receive one or more elongate bodily structures such as veins, arteries, capillaries, venules, nerves, ligaments, and the like. In one embodiment, the nonbiologic shell of the implant 50 is formed after imaging the subject tissue at the location of the implant to identify any elongate bodily structures at that location. The nonbiologic shell is manufactured to include the passages 53A-53C at the locations of the elongate structures of the subject body identified during imaging. Suitably, the passages 53A-53C are shaped and arranged to receive and/or themselves form the elongate structures therethrough in substantially the same orientation and arrangement as they previously extended through the host tissue at the same location. In one embodiment, the biologic portion of the implant 50 comprises pancreatic tissue and corresponding growth factors. The passages 53A-53C can suitably be shaped and arranged to rout the ductal network associated with the subject's gallbladder through the pancreatic implant 50. In certain embodiments, elongate biologic structures (e.g., ligaments, tendons, nerves, and the like) for grafting into the elongate structures of the subject body are grown on the nonbiologic shell of the implant 50 in the passages 53A-53C during incubation of the biologic material. Connections between the elongate biologic structures grown in the passages 53A-53C and the subject bodily structures are surgically established during the implantation procedure.

Figure 7:
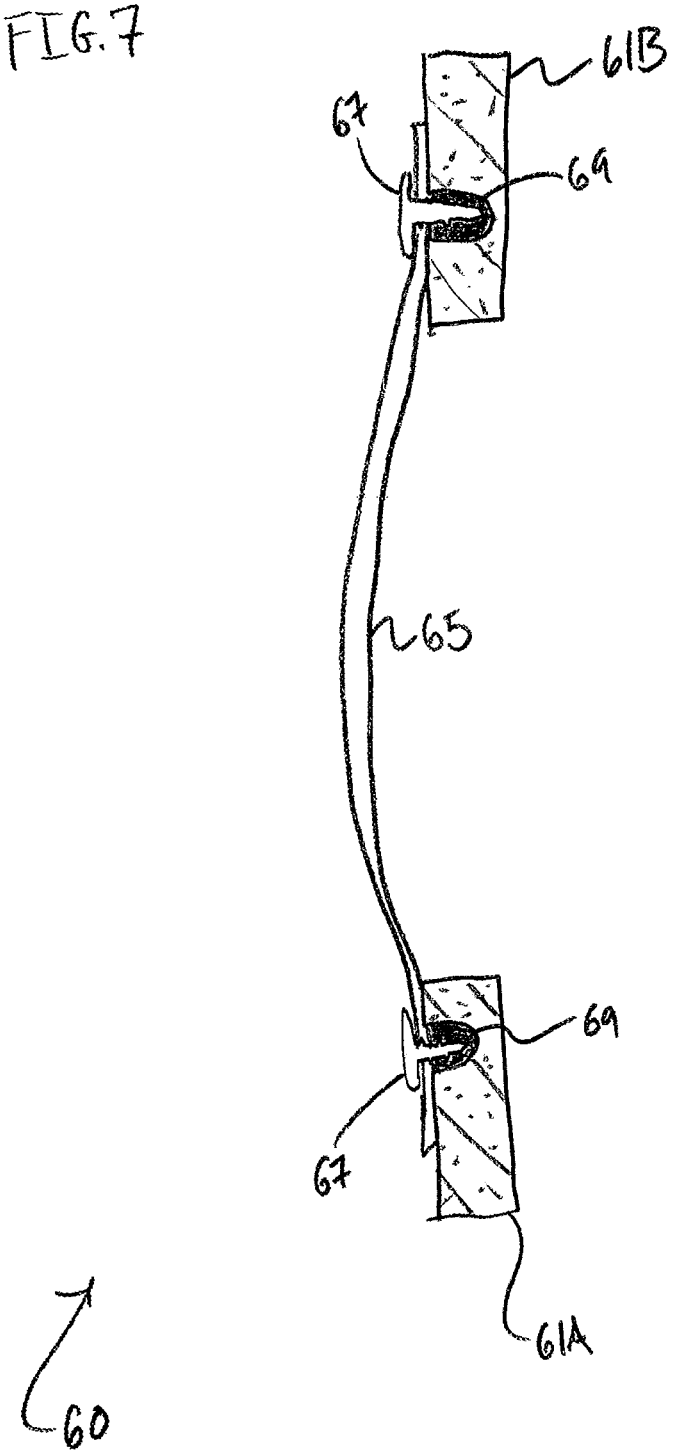
FIG. 7 is a schematic cross section of a bone-tendon-bone implant.

Referring to FIG. 7, another embodiment of an implant for replacing a portion of subject tissue (e.g., an ACL or other ligament) is generally indicated at reference number 60. The implant 60 includes a first bone implant 61A and a second bone implant 61B. Each bone implant 61A, 61B comprises a nonbiologic porous shell and a biologic material configured for forming a graft with bone tissue embedded in the pores of the shell. A tendon implant 65 is attached to each bone implant 61A, 61B. More specifically, opposite end portions of the tendon implant 65 are attached to the bone implants 61A, 61B to form a bone-tendon-bone implant, such as an ACL replacement implant. In the illustrated embodiment, the tendon implant 65 is attached to each bone implant 61A, 61B using a screw 67. The nonbiologic shell of the each bone implant 61A, 61B includes a cladding portion 69 that comprises a low porosity or non-porous non-biologic material. Thus the screw 67 may be configured to self-tap into the bone implant 61A, 61B through the cladded portion 69 to securely fasten the tendon implant 65 to the bone implant. Each bone implant 61A, 61B can be surgically inserted into the subject in the same manner as described above at a respective location for securing the tendon implant 65 between two subject bone locations. It is understood that a tendon implant comprising only one bone implant can be formed by removing one of the bone implants 61A, 61B. Likewise, the tendon could be replaced with, for example, a muscle or a ligament to form a bone-muscle or a bone-ligament implant, respectively.

Figure 8:
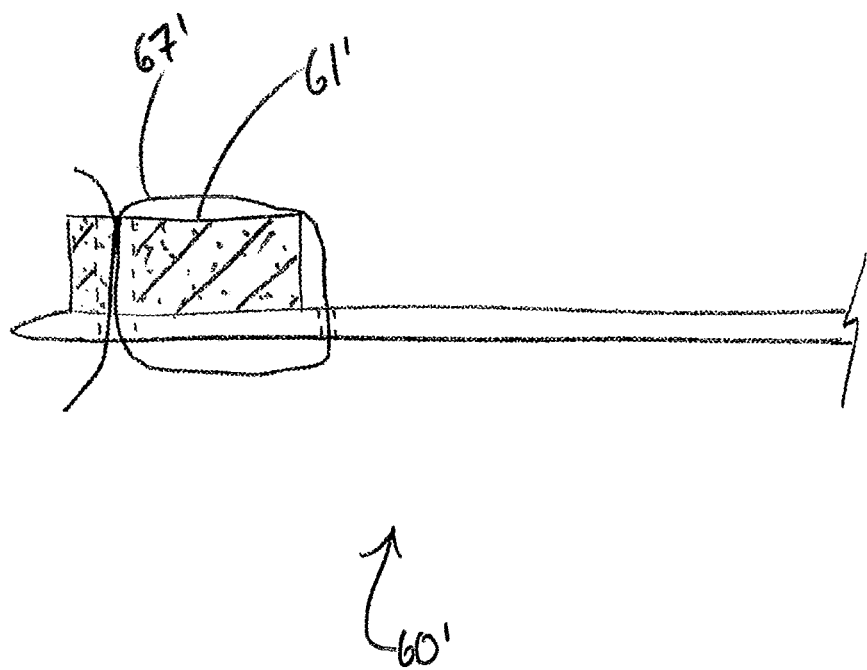
FIG. 8 is a schematic cross section of another embodiment of a bone-tendon implant.

Referring to FIG. 8, in another embodiment, an implant, generally indicated at 60', comprises a bone implant 61' and a tendon implant 65'. Each bone implant 61' comprises a nonbiologic porous shell and a biologic material configured for forming a graft with bone tissue embedded in the pores of the shell. Unlike the bone-tendon implant 60 of FIG. 7, the bone implant 61' is bound to the tendon implant 65' using a thread, wire, or suture 67'. Passages are formed in the bone implant 60' and the tendon implant 65' for receiving the thread or wire 67', and the thread is tied around the two implants to bind them together. Still other ways of preoperatively attaching a bone implant to a tendon implant, muscle implant, ligament implant, etc. may be used in other embodiments.

Figure 9:
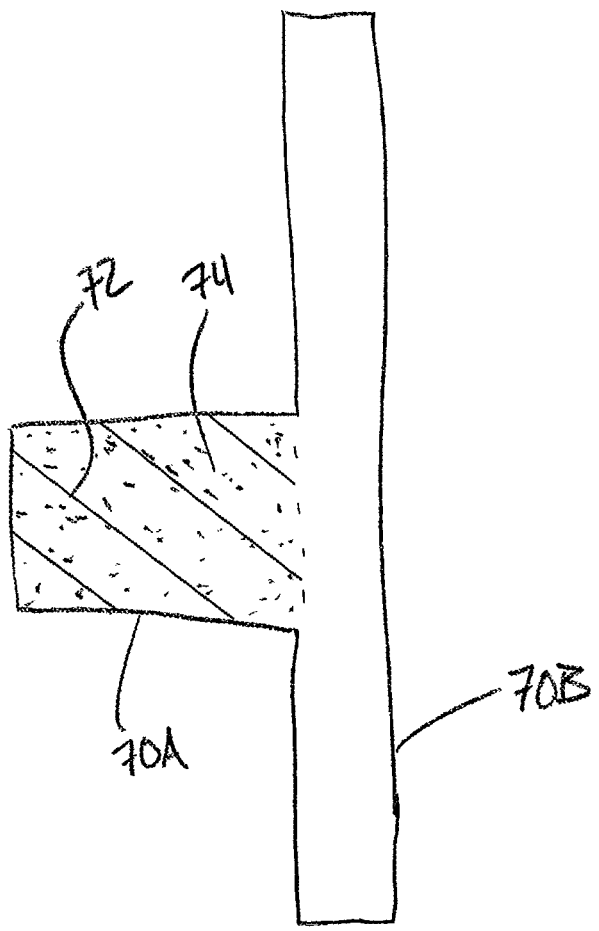
FIG. 9 is a schematic elevation of another embodiment of an implant.

Referring to FIG. 9, another embodiment of a bone implant is generally indicated at reference number 70. The bone implant 70 includes a graft portion 70A and a bone connection portion 70B. Like the implants discussed above, the graft portion 70A comprises a porous nonbiologic shell 72 and biologic materials 74 supported on the shell for encouraging tissue ingrowth through the porous shell to repair a subject bone with new tissue growth. The bone connection portion 70B comprises a connecting element configured for securing together pieces of fractured subject bone. For example, in one embodiment, the bone connection portion 70B comprises a bone rod; in other embodiments, the bone connection portion comprises a mending plate. In still other embodiments, other connecting elements can be used. Suitably, the nonbiologic shell 72 can be formed integrally with the connection portion 70B of the bone implant 70. For example, the shell 72 and the connection portion 70B may be formed together, of the same material, in the same additive manufacturing process. In the illustrated embodiment, the connection portion 70B of the implant is substantially nonporous to enhance the structural characteristics of the connection portion. In other embodiments, the nonbiologic shell 72 is formed separately from the bone connection element 70B, and the two pieces are fastened to one another using, for example, mechanical fasteners. In use, the bone connection element 70B to reconnect fractured portions of a subject bone in a manner known to those skilled in the art. The graft portion 70A of the implant 70 is positioned in subject bone tissue in the manner described above to form a bone graft within the reconnected bone portions.

Figure 10:
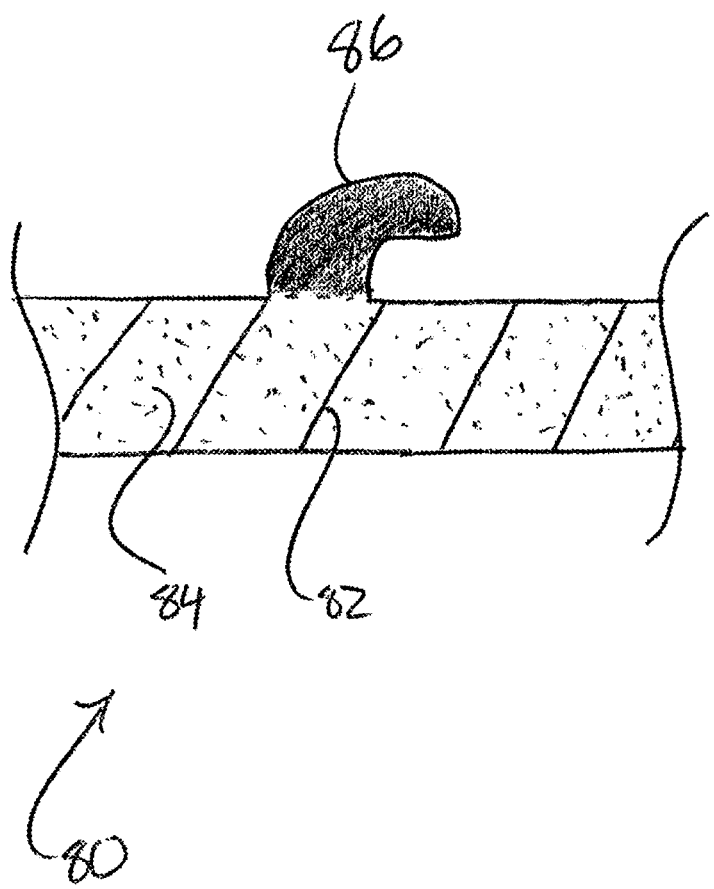
FIG. 10 is a fragmentary schematic elevation of another embodiment of an implant.

Referring to FIG. 10, another embodiment of a bone implant is generally indicated at reference number 80. The bone implant 80 includes nonbiologic porous shell 82 and biologic material 84 supported in the pores of the shell. In addition, the bone implant 80 includes a ligament anchoring structure 86 for intraoperatively anchoring a subject ligament to the bone implant. In the illustrated embodiment, the ligament structure 86 is a hook-shaped formation on an outer surface of the bone implant. In one embodiment, the ligament anchoring structure 86 is formed integrally with the nonbiologic shell 82 in an additive manufacturing process. In another embodiment, the ligament anchoring structure 86 is formed separately from the nonbiologic shell and is preoperatively attached to the nonbiologic shell (e.g., using a mechanical fastener). After the bone implant 80 is surgically placed in the subject bone a subject ligament can be fixed to the ligament anchoring structure 86 using a fastener, a binding, etc. In one or more embodiment, the bone implant 80 is configured to be anchored to the subject bone using a keel, fastener, binding, etc., before the ligament is anchored on the anchoring structure 86 so that the implant can immediately withstand the tensions in the ligament without becoming dislodged from the subject bone.

Figure 11:
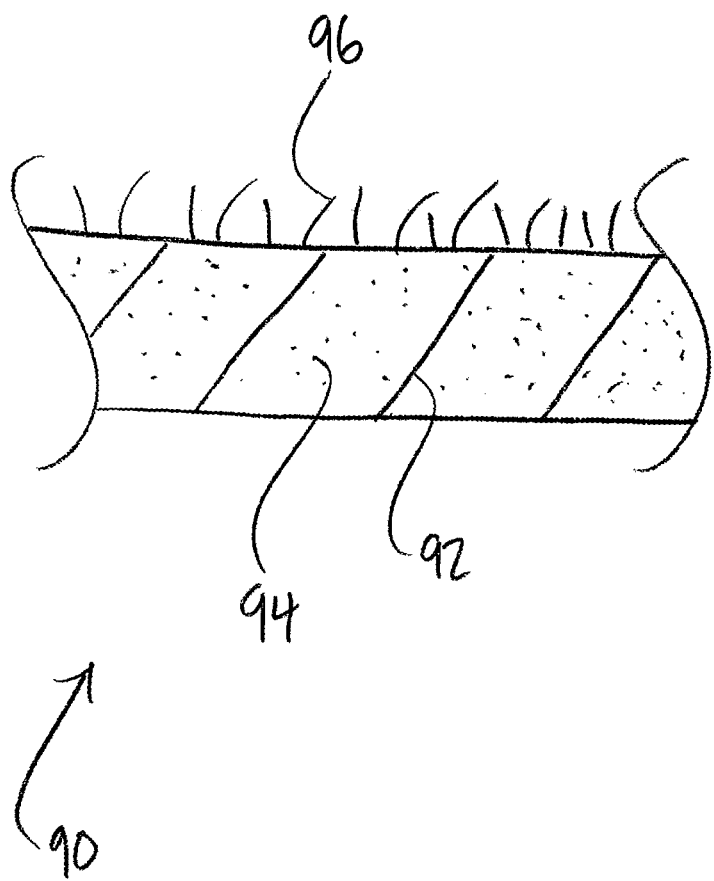
FIG. 11 is a fragmentary elevation of another embodiment of an implant.

Referring to FIG. 11, another embodiment of a bone implant is generally indicated at reference number 90. The bone implant 90 includes nonbiologic porous shell 92 and biologic material 94 supported in the pores of the shell. In addition, a biologic tissue anchoring formation 96 is formed along an outer surface of the bone implant. In the illustrated embodiment, the biologic tissue anchoring formation 96 comprises incubated Sharpey's fibers, but other biologic tissue anchoring formations can also be used in other embodiments. After the bone implant 90 is surgically placed in the subject, the Sharpey's fibers 96 grow into the musculature or other tissue adjacent the implant to anchor the tissue to the bone.

In one embodiment, an implant could be configured to repair or replace a portion or all of a rotator cuff. For example, an implant could include one or more bone implants for being grafted into the scapula, the clavicle, and/or the humerus. Each bone implant suitably comprises a nonbiologic shell and biologic bone graft material ingrown into the shell using incubation. Different regions of the shell can have different densities and different tissue orientations to match the densities of the implants to the subject bones and to provide structural support at locations where the implant attaches to rotator cuff tendons. The shells can include one or more tissue anchoring structures such as is shown in FIG. 10 for anchoring rotator cuff tendons and shoulder muscles to the bone implants. In addition or in the alternative, replacement rotator cuff tendons can be preoperatively attached to one or more bone implants as shown in FIGS. 7 and 8. In one or more embodiments, the replacement tendons themselves are formed by incubating tissue on a nonbiologic porous shell comprising a material having dynamic characteristics (e.g., flexibility, resilience) substantially matched to the tendon it is replacing. The density and porosity of the shell underlying the replacement tendon is suitably matched to that of the subject tendon being replaced.

In addition or in the alternative to the nonbiologic shells discussed above, an implant may comprise a collagen-based scaffold for the biologic material (e.g., bone graft material). In one embodiment, a scaffold can comprise a porous nonbiologic shell (e.g., a foam metal shell) and a collagen infrastructure scaffold. The collagen scaffold can suitably be denatured. The collagen would be attached to adhere to nonbiologic material, and then biologic material such as bone cells, precursors, osteocytes, osteoblast, osteoclast, and/or stem cells would be incubated on the collagen and nonbiologic shell.

Figure 12:
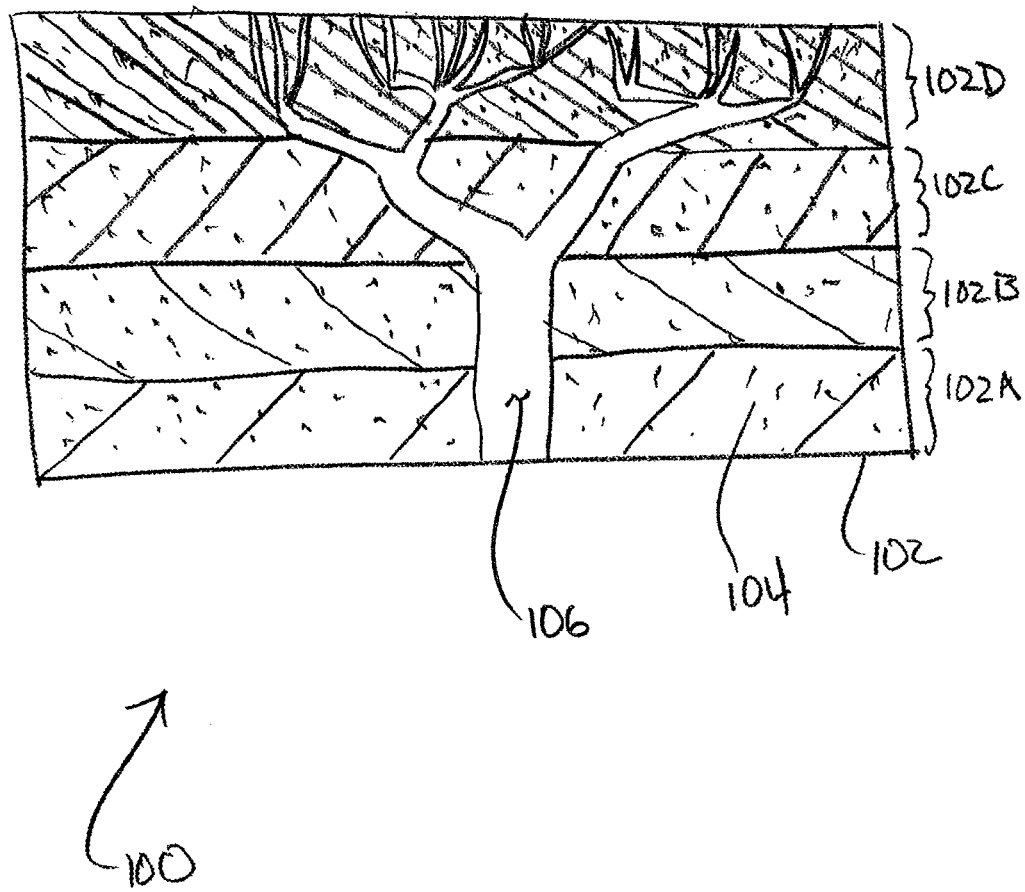
FIG. 12 is a schematic cross section of another embodiment of an implant.

Referring to FIG. 12, another embodiment of an implant is generally indicated at reference number 100. The implant 100 includes a nonbiologic porous shell 102 having a plurality of regions 102A-102D, each having different material characteristics (e.g., porosity, density, material type, etc.) to match the shell region to a corresponding tissue region of the subject. Biologic tissue material 104 is ingrown into the shell 102 for forming a graft with subject tissue when the implant 100 is implanted into the subject. In the illustrated embodiment, the shell defines a plurality of passages 106 for receiving vasculature of the subject at the location of the tissue implant. Suitably, the shape and arrangement of the vasculature passages 106 are established in an additive manufacturing process using three-dimensional modeling of the subject vasculature based on preoperative imaging of the subject tissue. As shown in FIG. 12, the passages 106 include large diameter passages for receiving relatively large diameter portions of arteries and/or veins, small diameter passages for receiving capillaries, and medium diameter passages for receiving connecting vasculature.

Figure 14:
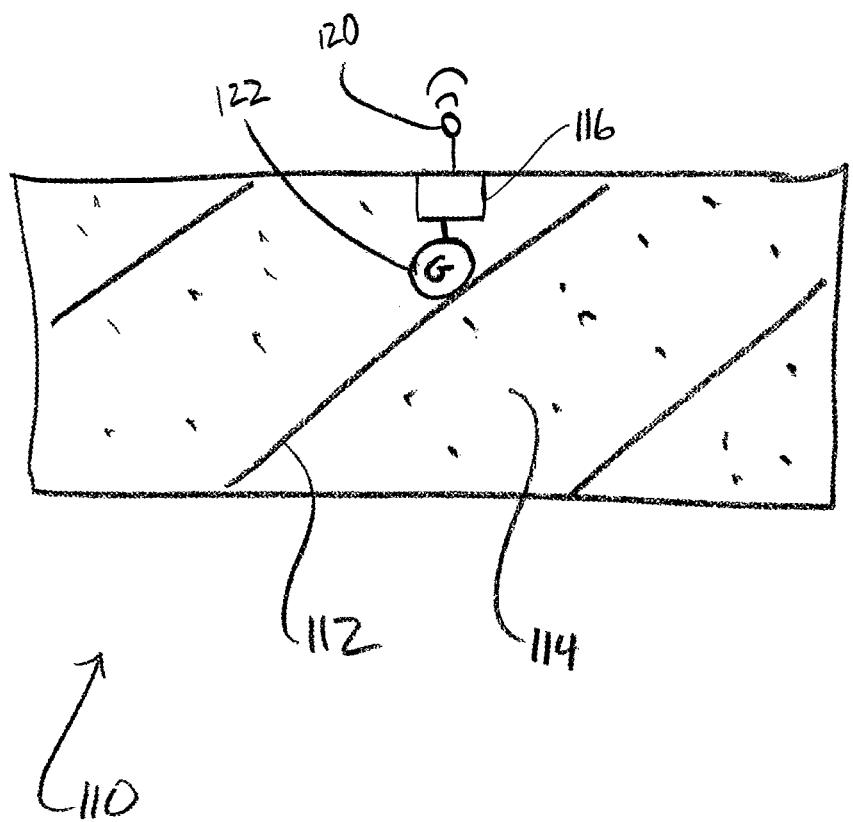
FIG. 14 is a schematic elevation of another embodiment of an implant shown wirelessly connected to a data processor.

Referring to FIG. 14, another embodiment of an implant is generally indicated at reference number 110. The implant 110 includes a nonbiologic porous shell 112 and a biologic material 114 embedded in the shell. In addition, the implant 110 comprises one or more sensors 116 that are preoperatively or intraoperatively mounted on the implant for sensing one or more parameters of the implant. For example, in certain embodiments, the sensors 116 comprise one or more of a chemical sensor (e.g., a pH sensor, etc.), a biological sensor (e.g., an analyte sensor), a thermal sensor (e.g., an RTD, a thermocouple, etc.), a mechanical sensor (e.g., a stress or strain gauge, etc.), or the like. Suitably, the sensors 116 are configured to sense parameters of the implant that are related to postoperative tissue ingrowth into the implant. For example, tissue ingrowth into the shell 112 may impart stress or strain on the shell that can be detected by a mechanical sensor. Likewise, tissue ingrowth may correspond to changes in temperature, chemical environment, or biological environment that are detectable using the sensors 116.

The sensors 116 are suitably connected to a data processor 118 (e.g., a laptop computer, a desktop computer, a mobile device such as a cellphone or a tablet computer, or the like) for receiving the data from the sensors and providing the data to a user (e.g., on a display). For example, in one or more embodiments, the sensors 116 are connected to a data processor via a wireless transmitter 120 that is mounted on the implant. In other embodiments, the implant 110 can include a wire connector (not shown) for connection to a cable of the data processor 118 that extends from the implant and is postoperatively accessible through a port in the skin of the patient. Suitably, the sensors 116 and any associated communications electronics are configured to draw power from a biomechanical or biochemical electrical generator 122. In other embodiments, however, the sensors 116 include a battery or capacitor that is wirelessly chargeable through the body of the subject (e.g., via an inductive coupling, etc.). In still other embodiments, the sensor and communications electronics can be powered using an external power device that is connectable to the implant through a port in the body of the subject.

Postoperative tissue ingrowth can also be determined in other ways. For example, in some embodiments, a practitioner can conduct a postoperative scan of the implant region to determine if the tissue density in the region has increased since surgery. Increased tissue density generally corresponds to ingrowth of tissue into the implant.

It may also be desirable to postoperatively evaluate the strength of the mechanical connection of the implant with the host tissue. In one method of evaluating the strength of the implant region, the practitioner can vibrate one of the implant and the host tissue and monitor a vibrational response (e.g., a vibrational frequency response, a vibrational amplitude response, a velocity response, etc.) of both the implant and the host tissue. If the vibrational responses of the host tissue and the implant are different and substantial relative motion between the implant and the host tissue is detected, this may provide an indication of relatively low mechanical connection strength between the host tissue and the implant. In another embodiment, the strength of the connection between the implant and the host tissue can be determined by detecting fluid at the interface between the implant and the host tissue.

It may also be desirable to postoperatively determine whether a nonbiologic shell of an implant has corroded. In one method of determining corrosion, a practitioner imparts a local electric charge at a portion of the subject body adjacent the implant. The charge is suitably configured to draw corroded particles of the nonbiologic shell toward the charged portion of the subject body. For example, corrosion of the nonbiologic shell can, in some embodiments, create loose cobalt-chromium in the subject body that can be drawn toward an electrically charged area adjacent the implant. After imparting the electrical charge for the desired amount of time, the practitioner detects the level of corroded particles in the area to determine the extent corrosion of the nonbiologic shell.

As can be seen implants comprising a nonbiologic porous shell and biologic materials supported on the shell can be implanted in tissue to both provide an immediate load-bearing structural repair of the tissue and facilitate regenerative tissue ingrowth for permanent repair of the tissue. Bone, in particular, may actually grow faster and more reproducibly into a nonbiologic shell than into allograft or artificial bone because the graft material does not have to decay in order for the bone tissue to grow. Bone ingrowth can begin as soon as the shell is implanted. And the self-supporting shell remains stable so that the new bone can be grown more rapidly and consistently. In conventional bone grafts, the required degradation of the graft material causes the bone growth to be comparatively unpredictable. This degradation cycle of 100% biologic tissue becomes problematic in allografts or treated tissues.

By scanning the subject tissue prior to implantation, the implant can be custom manufactured to match the porosity, curvature, shape, and thickness of the host tissue to form a uniform and contiguous replacement or repair structure. Cartilage or other types of tissues (tendons, muscles, ligaments, vasculature, etc.) could be grown on top of the implant using biologic stem cells, cartilage shells, fetal cartilage, fetal bone, etc. Imaging and shaping of the implants and subject tissue allows for precise shape matching between the implant and the subject tissue. In addition, the nonbiologic shell can be constructed to have multiple layers or regions that have different characteristics (porosity, density, etc.) that match characteristics of the layers or regions of tissue being replaced. This is feasible with the wide range of manufacturing technologies applicable to making the nonbiologic shell but is quite difficult to achieve using conventional grafting materials such as allografts. Where the tendons and ligaments attach to the implant, the additive manufacturing process allows for reducing the porosity to increase strength. And moreover, modeling and manufacturing the nonbiologic shell using additive manufacturing processes allows the surgeon to construct built-in passages for connecting the implant to vasculature and other bodily functions at the site of the implant.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An implant for being implanted in a subject, the implant comprising:
    a three-dimensional (3D) printed shell configured to be implanted in an organ having a first tissue with a first tissue porosity and a second tissue with a second tissue porosity, the shell comprising a nonbiologic material that is formed by 3D printing the shell having a first porous region having a first porosity corresponding with the first tissue porosity and a second porous region having a second porosity corresponding with the second tissue property, wherein the first porous region overlies the second porous region;
    a first type of tissue ingrown by incubation into pores of the first porous region of the shell, wherein the first type of tissue comprises cartilage tissue;
    a second type of tissue different from the first type of tissue ingrown by incubation into pores of the second porous region of the shell, wherein the second type of tissue comprises bone.

2. An implant as set forth in claim 1 wherein the shell has a density corresponding with a tissue density of the subject.

3. An implant as set forth in claim 1 further comprising a tissue attachment structure connected to the shell.

4. An implant as set forth in claim 1 wherein the shell defines a passage for receiving a body part of the subject.

5. An implant as set forth in claim 1 wherein the shell comprises a metal.

6. An implant as set forth in claim 5 wherein the shell comprises a metal foam.

7. An implant as set forth in claim 1 wherein the implant is shaped and arranged for being press fit into a hole in tissue of the subject.

8. An implant as set forth in claim 1 wherein the implant has first and second ends and sides that taper between the first and second ends.

9. An implant as set forth in claim 1 further comprising at least one anchoring projections extending from the shell and configured to anchoring the implant in the subject.

10. An implant as set forth in claim 1, wherein the first porous region of the shell has a first thickness configured to match a first tissue thickness of the first type of tissue having the first porosity and the second porous region of the shell has a second thickness configured to match a second tissue thickness of the second type of tissue having the second porosity.

11. An implant as set forth in claim 10, wherein the shell has proximal and distal ends, the first porous region of the shell extending from the proximal end to a position intermediate of the proximal and distal ends, the second porous region of the shell extending from the first porous region at the position intermediate of the proximal and distal ends to the distal end.

12. An implant as set forth in claim 1, wherein pores of the first porous region are in communication with pores of the second porous region.

* * * * *